United States Patent
Lu et al.

(10) Patent No.: US 10,568,890 B2
(45) Date of Patent: Feb. 25, 2020

(54) LACTATE-BASED FULVESTRANT OR FULVESTRANT DERIVATIVE OILY PREPARATION AND PREPARATION METHOD THEREOF

(71) Applicant: Xi'An Libang Pharmaceutical Co., Ltd, Xi'An (CN)

(72) Inventors: Wudang Lu, Shaanxi (CN); Weiping Yu, Shaanxi (CN); Tao Chen, Shaanxi (CN); Rui Cai, Shaanxi (CN)

(73) Assignee: XI'AN LIBANG PHARMACEUTICAL CO., LTD, Xi'An (CN)

( * ) Notice: Subject to any disclaimer, the term of this patent is extended or adjusted under 35 U.S.C. 154(b) by 0 days.

(21) Appl. No.: 14/389,532

(22) PCT Filed: Nov. 15, 2012

(86) PCT No.: PCT/CN2012/084685
§ 371 (c)(1),
(2) Date: Nov. 19, 2014

(87) PCT Pub. No.: WO2013/143299
PCT Pub. Date: Oct. 3, 2013

(65) Prior Publication Data
US 2015/0105357 A1 Apr. 16, 2015

(30) Foreign Application Priority Data
Mar. 31, 2012 (CN) .......... 2012 1 0093205

(51) Int. Cl.
| | | |
|---|---|---|
| A61K 31/565 | (2006.01) | |
| A61K 9/19 | (2006.01) | |
| A61K 47/44 | (2017.01) | |
| A61K 9/00 | (2006.01) | |
| A61K 31/045 | (2006.01) | |
| A61K 47/14 | (2017.01) | |

(52) U.S. Cl.
CPC .......... *A61K 31/565* (2013.01); *A61K 9/0019* (2013.01); *A61K 31/045* (2013.01); *A61K 47/14* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,389,681 A | 2/1995 | Galli | |
| 8,048,919 B2* | 11/2011 | Muse, Jr. ................. | A61K 9/10 514/546 |
| 8,324,194 B2* | 12/2012 | Fridman .............. | A61K 31/496 514/183 |
| 2001/0020016 A1 | 9/2001 | Evans et al. | |
| 2005/0287179 A1 | 12/2005 | Muse et al. | |
| 2009/0181068 A1* | 7/2009 | Dunn ................... | A61K 9/0024 424/426 |
| 2009/0227552 A1 | 9/2009 | Hooley et al. | |
| 2011/0027389 A1* | 2/2011 | Dunn ................... | A61K 9/0024 424/649 |
| 2012/0329766 A1 | 12/2012 | Evans et al. | |
| 2015/0105357 A1 | 4/2015 | Lu et al. | |

FOREIGN PATENT DOCUMENTS

| | | | |
|---|---|---|---|
| CN | 1553815 A | 12/2004 | |
| CN | 101347406 A | 1/2009 | |
| CN | 102600073 A | 7/2012 | |
| DE | 29 49 849 A1 | 6/1981 | |
| EP | 2 244 752 A2 | 11/2010 | |
| EP | 2 832 349 A1 | 2/2015 | |
| FR | 2803516 A1 * | 7/2001 | ........... A61K 9/0019 |
| GB | 1 225 979 A | 3/1971 | |
| JP | 2003-519659 | 6/2003 | |
| JP | 2004-534093 | 11/2004 | |
| JP | 2009-509942 | 3/2009 | |
| WO | WO 01/51056 A1 | 7/2001 | |
| WO | WO 2003/006064 A1 | 1/2003 | |
| WO | WO 2009/091737 A2 | 7/2009 | |
| WO | WO 2013/143299 A1 | 10/2013 | |

OTHER PUBLICATIONS

Rifkin et al., "Castor Oil as a Vehicle for Parenteral Administration of Steroid Hormones," Journal of Pharmaceutical Sciences, vol. 53, No. 8, Aug. 1964.*
Office Action for corresponding Japanese Application No. 2015-502058 dated Nov. 17, 2015.
Japan Pharmaceutical Excipients Council, Yakuji Nippo, Feb. 28, 2007 p. 645-647.
Japan Pharmaceutical Association, Yakuji Nippo, Sep. 8, 2006, p. 206.
Injectable solution the foundation, Nanzando, Aug. 27, 1998, p. 21-234.
Office Action from Canadian Patent Application No. 2,872,001 dated Feb. 17, 2016.
Written Opinion from International Application No. PCT/CN2012/084685 dated Feb. 28, 2013.
Office Action from Chinese Patent Application No. 201210093205.X dated Feb. 17, 2013.

(Continued)

*Primary Examiner* — Jared Barsky
(74) *Attorney, Agent, or Firm* — Alston & Bird LLP

(57) ABSTRACT

An oily formulation of fulvestrant or derivatives thereof and a method for producing the same. The oily formulation comprises: fulvestrant or derivatives thereof in an amount of 10 mg/ml to 170 mg/ml; a lactate compound in an amount of 5 to 80% of the total weight of the formulation; a vegetable oil or synthetic oil (ester); an analgesic; and an optional antioxidant.

5 Claims, 1 Drawing Sheet

(56) References Cited

OTHER PUBLICATIONS

Office Action from Chinese Patent Application No. 201210093205.X dated Jul. 9, 2013.
Grant Document from Chinese Patent Application No. 201210093205.X dated Jan. 1, 2014.
International Searching Authority, International Search Report for International Application No. PCT/CN2012/084685, dated Feb. 28, 2013, 8 pages; State Intellectual Property Office of the P.R.C, P.R.C.
Extended European Search Report from corresponding European Patent Application No. 12872463.0 dated Aug. 4, 2015.
Office Action for Japanese Application No. 2015-502058 dated Jul. 12, 2016.
Xiao, S. et al., "Manual of Latest National Standards of Pharmaceutic Adjuvants"; 2006; p. 590.
Office Action for European Application No. 12872463.0 dated Aug. 3, 2018.

\* cited by examiner

LACTATE-BASED FULVESTRANT OR FULVESTRANT DERIVATIVE OILY PREPARATION AND PREPARATION METHOD THEREOF

FIELD OF TECHNOLOGY

The present application belongs to the field of pharmaceutic oily formulations for injection, and relates to a lactate-based oily formulation of fulvestrant or derivatives thereof and a method for producing the same. Such drugs can be used in the treatment of breast cancer in postmenopausal women.

BACKGROUND ART

Currently, breast cancer is one of the prevalent malignancies in women, and mainly has two characteristics. First, with the increasing seriousness of pollution in human survival environment, the incidence rate of breast cancer shows remarkable rising tendency, and has become the first of female malignancies; second, with the widespread use of modern diagnosis and treatment techniques, more and more breast cancer patients can be found in time at the early stage of outbreak, and life cycles of the breast cancer patients are prolonged by advanced treatment methods so that the death rate decreases significantly. Through a hundred years of exploration and development of treatment methods of breast cancer, by so far, there are four main approaches for clinical treatment of breast cancer: operation, radiotherapy, chemotherapy and endocrinotherapy (operative therapy and drug treatment). In particular, the establishment of endocrine drug therapy results in a breakthrough in the breast cancer treatment.

In 1970s, the appearance of tamoxifen on the market consolidates a landmark in endocrine drug treatment of breast cancer. In 1990s, due to the appearance of third-generation aromatase inhibitor (AIs), the endocrine drug treatment of breast cancer enters a new era. Currently, the typical clinical drugs include tamoxifen (TAM), toremifene (TOR), raloxifene, anastrozole (rimidex), letrozole (femara), exemestane (aromasin), and estrogen inhibitor fulvestrant and relevant derivatives thereof. Fulvestrant is an excellent representative thereof, which is a unique antiestrogenic drug that has completed full clinical trials at first. As compared to TAM, its affinity to a receptor (ER) is 100 times higher, without action to weaken estrogen. This drug was approved by U.S. FDA on April, 2002. In 2007, Perey et al., Swiss scholars, reported the experiment results of Phase II trial of SGCCRT. They stated that there was no significant difference between fulvestrant and exemestane used respectively as replacement drugs for treating advanced breast cancer patients (postmenopausal) having experienced treatment failure of first-line non-steroid drugs in terms of overall response rate (37% vs 28%), clinical benefit rate (CBR) and side effects. This indicates that fulvestrant can be used as a drug for treating advanced breast cancer patients (postmenopausal) having experienced treatment failure of first-line non-steroid drugs. Currently, the fulvestrant injection applied in clinic was developed by Astrazeneca Co., under the trade name of FASLODEX, which entered the Chinese market in 2010. The formula thereof mainly used ethyl alcohol and benzyl alcohol as cosolvents, and benzyl benzoate and castor oil as dispersants, and had many adverse events in clinical use.

Lactate compounds are mostly ester substances generated by reaction of lactic acid and hydroxyl-containing compounds. Currently, the liquid compounds which are useful in pharmaceutical industries mainly include ethyl lactate, propyl lactate, butyl lactate and isopentyl lactate, and ethyl lactate is favorite because of weakest irritation.

Ethyl lactate, also named ethyl α-hydroxylpropionate, a colorless transparent liquid having formula $C_5H_{10}O_3$, is an important raw material for medication production. Ethyl lactate is non-toxic, well soluble, non-volatile, fruity and easily biodegradable and soluble in water, alcohols, ethers, ketones and some oils (esters), and it is a substitute for toxic solvents (halogenated hydrocarbons, ethers) widely used in current pharmaceutical industries. In traditional pharmaceutical industries, ethyl lactate can be used as a lubricant for compressed tablets and an intermediate of pindolol drugs, and also can be used for transdermal formulations and injective formulations ("Manual of Latest National Standards of Pharmaceutic Adjuvants", Sangui XIAO et al., 2006, P590). Therefore, ethyl lactate is worthy of development in pharmaceutical industries, and is a "green solvent" with a good prospect of application. The invention is mainly to develop an oily formulation for intramuscular injection using lactates as a cosolvent for fulvestrant or relevant derivatives thereof.

SUMMARY OF THE INVENTION

The object of the invention is to provide formulae of a lactate-based oily formulation of fulvestrant or derivatives thereof.

The object of the invention is to provide a method for producing a lactate-based oily formulation of fulvestrant or derivatives thereof.

The object of the invention is further to provide the pharmacokinetic characteristics of such formulation in rats.

The formulation of the invention comprises: (1) a target compound: fulvestrant or relevant derivatives thereof; (2) a cosolvent: a lactate substance; (3) an analgesic; (4) a dispersant; and optionally, (5) an antioxidant.

Specifically, the formulation of the invention comprises the following components:

| Name | Proportion |
| --- | --- |
| fulvestrant or derivatives thereof | 10-170 mg |
| lactate compound | 0.05-0.80 ml |
| analgesic | 3-5 mg/30-50 µl |
| dispersant | balanced to 1 ml | wherein said fulvestrant or derivatives thereof in the invention has the following structure:

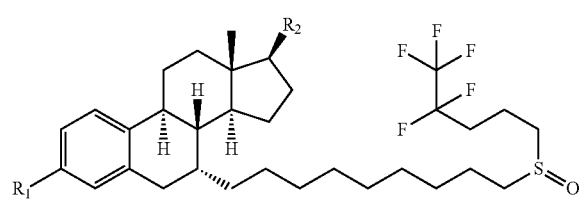

1) both of $R_1$ and $R_2$ may be —OH;
2) one of $R_1$ and $R_2$ may be —H, —O—CO—R, —CO—R or —O—R, and the other one should be —OH.

The fulvestrant or derivatives thereof in the invention may be one of the above compound or a mixture thereof, and fulvestrant (i.e., both of $R_1$ and $R_2$ may be —OH) is preferable in the formula.

The cosolvent in the invention is mainly lactate substances, which has the following basic structure:

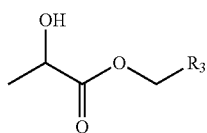

R₃ may be an alkyl group having various carbon chain length (such as —CH₃, —C₂H₅, —C₃H₇ or the like), or may be a substituent containing double bond, triple bond, benzene ring, hydroxyl or carbonyl.

The cosolvent in the invention may be one, or a mixture of two or more of them. In this study, one, or a mixture of two or more of ethyl lactate, propyl lactate and butyl lactate is preferable, and ethyl lactate is the most preferable.

The analgesic in the invention is selected from one, or a mixture of two or more of benzyl alcohol, trichloro-tert-butanol, lidocaine (free base), procaine (free base), tetracaine (free base), ropivacaine (free base), mepivacaine (free base), articaine (free base), bupivacaine (free base), propofol, propofol derivatives, tramadol, lappaconitine, 1-tetrahydropalmatine, pentazocine, cyclobutylmethyl dihydroxymorphina, fentanyl and derivatives thereof; preferably, one, or a mixture of two or more of benzyl alcohol, trichloro-tert-butanol, lidocaine (free base), procaine (free base), tetracaine (free base), ropivacaine (free base), mepivacaine (free base), articaine (free base) and bupivacaine (free base); most preferably, one, or a mixture of two or more of benzyl alcohol, trichloro-tert-butanol and ropivacaine (free base).

The dispersant in the invention is selected from:

1) one, or a mixture of two or more of castor oil, polyoxyethylene castor oil (35, 40), hydrogenated castor oil and sulfonated castor oil at any ratio;

2) a mixture of one, or a mixture of two or more of castor oil, polyoxyethylene castor oil (35, 40), hydrogenated castor oil and sulfonated castor oil with one, two or more of other oils (esters) (purified for injection) at any ratio, wherein the other oils (esters) are soybean oil, corn oil, olive oil, rapeseed oil, sunflower oil, sesame oil, palm oil, sea buckthorn oil, fish oil, seal oil, fur seal oil, shark oil, zedoary oil, coix seed oil, garlic oil, safflower oil, zanthoxylum oil, hemlock parsley oil, artemisia annua oil, wintergreen oil, evening primrose oil, angelica oil, ginger oil, nepeta oil, forsythia oil, eucalyptus oil, perilla oil, orange peel oil, vitex oil, rose oil, peppermint oil, capillary artemisia oil, fennel oil, turpentine wood oil, clove oil, anise oil, thyme oil, cinnamon oil, artemisia argyi oil, perilla oil, turmeric oil, melaleuca oil, lavender oil, costus oil, patchouli oil, verbena oil, wormwood oil, clary sage oil, rhizoma atratylodes oil, myrtle oil, lemon oil, citrus aurantium oil, basil oil, perilla leaf oil, pine tar, coconut oil, fructus amomi oil, olive oil, citronella oil, geranium oil, elsholtzia ciliata oil, spearmint oil, taxus oil, patchouli oil, styrax oil, blackcurrant oil, schisandra oil, acorus gramineus oil, cnidium oil, phellodendron fruit oil, lavender oil, rosemary oil, bergamot oil, sandalwood oil, carrot seed oil, cedarwood leaf oil, celery seed oil, origanum oil, citronellal oil, coriander oil, neroli oil, nutmeg oil, onion oil, sandalwood oil, marigold oil, thyme oil, ylang oil, glycerol triacetate, glycerol monoacetate, benzyl benzoate, isopropyl myristate, tributyl citrate, ethyl succinate, dimethyl succinate, alkyl (C₁₂-C₁₅) benzonate, ethyl heptanoate, diethyl sebacate, triethyl citrate, pentaerythritol phthalate, allyl cyclohexanepropionate, ethyl benzoate, benzyl phenylacetate, ethyl caprylate, butylene gallate, ethyl gallate, propyl gallate, methyl myristate, isopentyl isovalerate, ethyl isovalerate, isopentyl palmitate, ethyl valerate, ethyl propionate, isopentyl propionate, benzyl propionate, methyl methacrylate, 2-hydroxyethyl methacrylate, N-methyl-2-pyrrolidone, geranyl formate, propylene carbonate, propanediol carbonate, diethyl malonate, allyl hexanoate, ethyl hexanoate, geranyl butyrate, benzyl butyrate, isopentyl butyrate, butyl butyrate, ethyl butyrate, cinnamyl acetate, geranyl acetate, benzyl acetate, butyl acetate, ethyl acetate, oleic acid and oleates.

Preferably, the dispersant in the invention is:

1) one, or a mixture of two or more of castor oil, polyoxyethylene castor oil (35, 40), hydrogenated castor oil and sulfonated castor oil at any ratio;

2) a mixture of one, or a mixture of two or more of castor oil, polyoxyethylene castor oil (35, 40), hydrogenated castor oil and sulfonated castor oil with one, two or more of other oils (esters) (purified for injection) at any ratio, wherein the other oils (esters) include soybean oil, corn oil, olive oil, rapeseed oil, sunflower oil, and sesame oil.

Preferably, the formula of the formulation of the invention is:

| Name | Proportion |
| --- | --- |
| fulvestrant or derivatives thereof | 10-170 mg |
| lactate compound | 0.05-0.80 ml |
| analgesic | 3-5 mg/30-50 μl |
| dispersant | balanced to 1 ml |

More preferably, the formula of the formulation of the invention is:

| Name | Proportion |
| --- | --- |
| fulvestrant or derivatives thereof | 25-100 mg |
| lactate compound | 0.15-0.50 ml |
| analgesic | 3-5 mg/30-50 μl |
| dispersant | balanced to 1 ml |

Specifically, the formula of the formulation of the invention is:

| Name | Proportion |
| --- | --- |
| 1) | |
| fulvestrant | 10 mg |
| ethyl lactate | 0.05 ml |
| trichloro-tert-butanol | 3 mg |
| glycerol triacetate | 0.35 ml |
| castor oil | balanced to 1 ml |
| 2) | |
| fulvestrant | 170 mg |
| ethyl lactate | 0.80 ml |
| benzyl alcohol | 50 μl |
| castor oil | balanced to 1 ml |
| 3) | |
| fulvestrant | 25 mg |
| ethyl lactate | 0.15 ml |
| trichloro-tert-butanol | 3 mg |
| ethyl oleate | 0.25 ml |
| castor oil | balanced to 1 ml |

-continued

| Name | Proportion |
|---|---|
| 4) | |
| fulvestrant | 100 mg |
| ethyl lactate | 0.50 ml |
| benzyl alcohol | 50 μl |
| castor oil | balanced to 1 ml |
| 5) | |
| fulvestrant | 60 mg |
| ethyl lactate | 0.30 ml |
| benzyl alcohol | 50 μl |
| castor oil | balanced to 1 ml |
| 6) | |
| fulvestrant | 50 mg |
| ethyl lactate | 0.25 ml |
| benzyl alcohol | 50 μl |
| castor oil | balanced to 1 ml |
| 7) | |
| fulvestrant | 50 mg |
| ethyl lactate | 0.35 ml |
| trichloro-tert-butanol | 5 mg |
| mixed oil | balanced to 1 ml |

Note:
the mixed oil refers to a mixture of castor oil and soybean oil (volume ratio: 1:1).

| Name | Proportion |
|---|---|
| 8) | |
| fulvestrant | 70 mg |
| ethyl lactate | 0.50 ml |
| trichloro-tert-butanol | 5 mg |
| mixed oil | balanced to 1 ml |

Note:
the mixed oil refers to a mixture of castor oil and soybean oil (volume ratio: 1:1).

| Name | Proportion |
|---|---|
| 9) | |
| fulvestrant | 110 mg |
| ethyl lactate | 0.80 ml |
| trichloro-tert-butanol | 5 mg |
| mixed oil | balanced to 1 ml |

Note:
the mixed oil refers to a mixture of castor oil and peanut oil (volume ratio: 1:1).

| Name | Proportion |
|---|---|
| 10) | |
| fulvestrant | 40 mg |
| ethyl lactate | 0.30 ml |
| trichloro-tert-butanol | 5 mg |
| glycerol triacetate | 0.10 ml |
| mixed oil | balanced to 1 ml |

Note:
the mixed oil refers to a mixture of castor oil and sesame oil (volume ratio: 1:1).

| Name | Proportion |
|---|---|
| 11) | |
| fulvestrant | 50 mg |
| butyl lactate | 0.30 ml |
| trichloro-tert-butanol | 5 mg |
| glycerol triacetate | 0.10 ml |
| castor oil | balanced to 1 ml |
| 12) | |
| fulvestrant | 75 mg |
| butyl lactate | 0.40 ml |
| benzyl alcohol | 50 μl |
| castor oil | balanced to 1 ml |
| 13) | |
| fulvestrant | 45 mg |
| butyl lactate | 0.40 ml |
| trichloro-tert-butanol | 5 mg |
| mixed oil | balanced to 1 ml |

Note:
the mixed oil refers to a mixture of castor oil and soybean oil (volume ratio: 1:1).

The invention also provides a method for producing the formulation, comprising the following steps:

Method I:

A. formulation production: a precisely weighed amount of one, or a mixture of two or more of fulvestrant or derivatives thereof is dissolved in a volume of a lactate compound, and sonicated or swirled until the substances are completely dissolved to obtain a solution 1; an antioxidant (optional) and an analgesic are added into an amount of a dispersant (one, or a mixture of two or more of vegetable oils or synthetic oils (esters)), sonicated or swirled until totally dissolved, added to the solution 1, finally added to a volume of 1 ml with the dispersant, and uniformly mixed by sonication or swirl to produce a desired solution;

B. sterile packaging: the produced solution is passed through a 0.45 μm organic membrane/nylon membrane under a sterile condition to remove impurities, sterilized through a 0.22 μm organic membrane/nylon membrane, and then dispensed into vials, filled with sterilized nitrogen, plugged and capped to obtain the oily formulation of fulvestrant or derivatives thereof.

Method II:

A. sterile formulation production: a precisely weighed amount of one, or a mixture of two or more of fulvestrant or derivatives thereof, an antioxidant (optional) and an analgesic are dissolved in a volume of a lactate compound, sonicated or swirled until the substances are completely dissolved, passed through a 0.45 μm organic membrane/nylon membrane under a sterile condition to remove impurities, and sterilized through a 0.22 μm organic membrane/nylon membrane; a dispersant (one, or a mixture of two or more of vegetable oils or synthetic oils (esters)) is subjected to dry heat sterilization at 180° C. or filtered through a 0.22 μm organic membrane/nylon membrane for sterilization; the sterile lactate solution containing substances and the dispersant are mixed uniformly to produce the sterile formulation;

B. formulation packaging: the produced sterile solution is dispensed into vials, filled with sterilized nitrogen, plugged and capped to obtain the oily formulation of fulvestrant or derivatives thereof.

Method III:

A. formulation production: a precisely weighed amount of fulvestrant or derivatives thereof, an antioxidant (optional) and an analgesic are dissolved in a volume of a lactate compound, sonicated or swirled until the substances are completely dissolved; a vegetable oil (one, or a mixture of two or more of vegetable oils or synthetic oils (esters)) is added to make 1 ml, and sonicated or swirled for 30 min to be well mixed;

B. sterile packaging: the produced solution is passed through a 0.45 μm organic membrane/nylon membrane under a sterile condition to remove impurities, sterilized through a 0.22 μm organic membrane/nylon membrane, dispensed into vials, filled with sterilized nitrogen, plugged and capped to obtain the oily formulation of fulvestrant or derivatives thereof.

Preferably, the production method of the invention comprises the following steps:

A. formulation production: a precisely weighed amount of fulvestrant or derivatives thereof, an antioxidant (optional) and an analgesic are dissolved in a volume of a lactate compound, sonicated or swirled until the substances are completely dissolved; a vegetable oil (one, or a mixture of two or more of vegetable oils or synthetic oils (esters)) is added to make 1 ml, and sonicated or swirled for 30 min to be well mixed;

B. sterile packaging: the produced solution is passed through a 0.45 μm organic membrane/nylon membrane under a sterile condition to remove impurities, sterilized through a 0.22 μm organic membrane/nylon membrane, dispensed into vials, filled with sterilized nitrogen, plugged and capped to obtain the oily formulation of fulvestrant or derivatives thereof.

The optional antioxidant shown in the production method may be: one, or a mixture of two or more of Vitamin A ester compounds, Vitamin E ester compounds, butyl hydroxylanisole and dibutyl hydroxyltoluene.

The formulation of the invention is a pharmaceutic formulation for injection.

The formulation of the invention is used in the production of drugs for treating breast cancer.

The oily formulation of fulvestrant according to the invention has the following characteristics:

1. The invention is the first to propose the use of lactate substances as a cosolvent in the production of intramuscular injections of fulvestrant, an anti-breast cancer drug, and to carry out the study on pharmacokinetics of such formulation in rats.

2. The invention is the first to propose the use of castor oil and relevant derivatives thereof (mainly including polyoxyethylene castor oil (35, 40), hydrogenated castor oil, sulfonated castor oil) as a dispersant in combination with other oils (esters), including soybean oil, corn oil, olive oil, rapeseed oil, sunflower oil, palm oil, sea buckthorn oil, fish oil, seal oil, fur seal oil, sesame oil, shark oil, zedoary oil, coix seed oil, garlic oil, safflower oil, zanthoxylum oil, hemlock parsley oil, artemisia annua oil, wintergreen oil, evening primrose oil, angelica oil, ginger oil, nepeta oil, forsythia oil, eucalyptus oil, perilla oil, orange peel oil, vitex oil, rose oil, peppermint oil, capillary artemisia oil, fennel oil, turpentine wood oil, clove oil, anise oil, thyme oil, cinnamon oil, artemisia argyi oil, perilla oil, turmeric oil, melaleuca oil, lavender oil, costus oil, patchouli oil, verbena oil, wormwood oil, clary sage oil, rhizoma atratylodes oil, myrtle oil, lemon oil, citrus aurantium oil, basil oil, perilla leaf oil, pine tar, coconut oil, fructus amomi oil, olive oil, citronella oil, geranium oil, elsholtzia ciliata oil, spearmint oil, taxus oil, patchouli oil, styrax oil, blackcurrant oil, schisandra oil, acorus gramineus oil, cnidium oil, phellodendron fruit oil, lavender oil, rosemary oil, bergamot oil, sandalwood oil, carrot seed oil, cedarwood leaf oil, celery seed oil, origanum oil, citronellal oil, coriander oil, neroli oil, nutmeg oil, onion oil, sandalwood oil, marigold oil, thyme oil, ylang oil, glycerol triacetate, glycerol monoacetate, benzyl benzoate, isopropyl myristate, tributyl citrate, ethyl succinate, dimethyl succinate, alkyl ($C_{12}$-$C_{15}$) benzonate, ethyl heptanoate, diethyl sebacate, triethyl citrate, pentaerythritol phthalate, allyl cyclohexanepropionate, ethyl benzoate, benzyl phenylacetate, ethyl caprylate, butylene gallate, ethyl gallate, propyl gallate, methyl myristate, isopentyl isovalerate, ethyl isovalerate, isopentyl palmitate, ethyl valerate, ethyl propionate, isopentyl propionate, benzyl propionate, methyl methacrylate, 2-hydroxyethyl methacrylate, N-methyl-2-pyrrolidone, geranyl formate, propylene carbonate, propanediol carbonate, diethyl malonate, allyl hexanoate, ethyl hexanoate, geranyl butyrate, benzyl butyrate, isopentyl butyrate, butyl butyrate, ethyl butyrate, cinnamyl acetate, geranyl acetate, benzyl acetate, butyl acetate, ethyl acetate, oleic acid and oleate derivatives. The difficulty that it is difficult to use other oils (esters) such as soybean oil alone as a dispersant in the oily formulations of fulvestrant has been solved.

3. The invention has carried out cosolvent screening experiment in vitro, test of miscibility of solvents in vitro, screening experiment of drug dissolution stability in vitro (4° C.), irritation experiment of topical injection in animals, experiment of viscosity, experiment of in vivo kinetics in animals, to analyze and screen formulae comprehensively.

4. The invention uses lactates, in particular ethyl lactate, as a solvent in the production of the oily formulation of fulvestrant. Ethyl lactate is a "green solvent" having highly exploitation value and application prospect in pharmaceutical industry, and the degradation products thereof have existed in vivo or are prone to metabolism. When the content of ethyl lactate in a pharmaceutic formulation is 20%-50%, the study of pharmacokinetics in animal experiments shows that the finished formulation thereof is characterized by high release speed and long release duration; moreover, the degradation in vivo of ethyl lactate is slow and the irritation thereof is decreased as compared with ethyl alcohol, which facilitates to the improvement of patient compliance.

5. The invention is the first to propose the use of trichloro-tert-butanol, lidocaine (free base), procaine (free base), tetracaine (free base), ropivacaine (free base), mepivacaine (free base), articaine (free base), bupivacaine (free base), propofol, propofol derivatives, tramadol, lappaconitine and derivatives thereof, L-tetrahydropalmatine, pentazocine, cyclobutylmethyl dihydroxymorphina, fentanyl and derivatives thereof as analgesics in the oily formulation of fulvestrant.

6. When the dispersant (one, or a mixture of two or more of castor oils or castor oil derivatives) is no lower than 50%, the oily formulation of fulvestrant according to the invention has a drug content per unit volume of up to 100 mg/ml. When it is administered according to the body weight, the volume of administration can be significantly reduced without shortening drug release duration, and the clinical patient compliance can be improved remarkably.

7. Various fulvestrant formulations of the invention can be produced by those skilled in the art in accordance with conventional pharmaceutical methods and equipments. The formulation process is simple and easy to operate.

DETAILED DESCRIPTION OF EMBODIMENT

Figure 1:
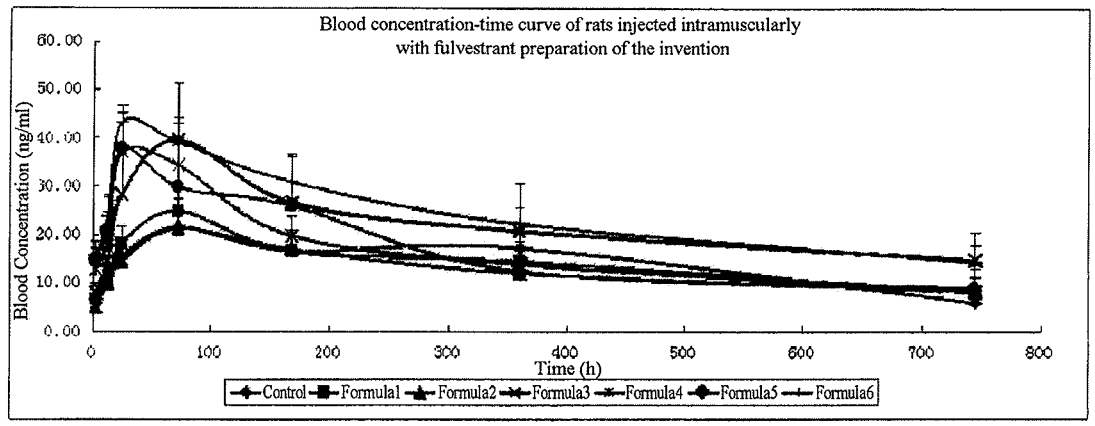
FIG. 1: A curve of blood concentration versus time.

The invention is further illustrated by the following Experimental examples and Examples without limiting thereto.

Experimental Example 1. Solubility Test of Fulvestrant in Some Solvents

Laboratory Instruments and Medications

Vortex mixer, ultrasonic cleaner, magnetic stirrer, HPLC, manual pipettes of various specifications with assorted tips, and tip boxes, 7 ml vials with assorted stoppers, and aluminium caps, liquid nitrogen cylinder and corresponding sterilization devices, and steam pressure disinfector.

Fulvestrant raw drug, supplied from No. 2 Pharmaceutical Factory of Xian Libang Pharmaceutical Co., Ltd., batch number: 080701; soybean oil, supplied from No. 1 Pharmaceutical Factory of Xian Libang Pharmaceutical Co., Ltd.; corn oil, North China Pharmaceutical Group, Kangxin Co., Ltd, batch number: 081002; ethyl lactate, Sinopharm Chemical Reagent Co., Ltd., batch number: T20071109; butyl lactate, Sinopharm Chemical Reagent Co., Ltd.; benzyl benzoate, Shanghai SSS Reagent Co., Ltd., batch number: 20030109; ethyl oleate, Shanghai Feixiang Chemical Factory; glycerol triacetate, Sinopharm Chemical Reagent Co., Ltd., batch number: F20100202; castor oil, ChengDu Kelong Chemical Reagent Company, batch number: 20061228; sesame oil, Xian Xiangzheng Foods Industry Co., Ltd., batch number: 20110701.

Into five vials of 7 ml each, an appropriate amount of fulvestrant raw drug was weighed precisely, and then 0.2-0.5 ml of ethyl lactate, butyl lactate, benzyl lactate, ethyl acetate, and isopentyl acetate were added respectively, and the dissolution status of the drug was monitored. If it was dissolved completely, the addition of the drug was resumed to reach a saturated state. Nitrogen was introduced, and the vials were kept airtight and free of light for 1-2 days to reach a dissolution-precipitation balance. Samples to be tested were made using absolute ethyl alcohol as the diluent, and respective contents therein were detected by HPLC to calculate the solubilities of fulvestrant raw drug in different solvents. The results were shown in Table 1.

TABLE 1

| | Solubilities of fulvestrant raw drug in different solvents (25° C.) | | | | | |
|---|---|---|---|---|---|---|
| No. | Menstruum name | Addition amount | Menstruum amount | Appearance | Solubility | Note |
| 1 | ethyl lactate | 180.87 mg | 0.5 ml | little precipitation | 303.28 mg/ml | slight heating |
| 2 | butyl lactate | 50.69 mg | 0.2 ml | little precipitation | 223.28 mg/ml | slight heating |
| 3 | ethyl acetate | 57.25 mg | 0.3 ml | little precipitation | 158.37 mg/ml | |
| 4 | isopentyl acetate | 32.97 mg | 0.5 ml | little precipitation | 50.98 mg/ml | |
| 5 | benzyl propionate | 14.40 mg | 0.5 ml | much precipitation | 4.34 mg/ml | |

The experimental results show that the solubility of fulvestrant was more than 100 mg/ml in each of ethyl lactate, butyl lactate and ethyl acetate; ethyl lactate was the best, butyl lactate comes second, followed by ethyl acetate in the solubility. Moreover, as compared with butyl lactate and ethyl acetate, the irritation of ethyl lactate was weak, and thus the study is primarily carried out using ethyl lactate as a cosolvent for fulvestrant in the invention.

Experimental Example 2. Test of Miscibility of Formulae In Vitro

Ethyl lactate was mixed with ethyl oleate, glycerol triacetate, benzyl benzoate, castor oil, sesame oil, soybean oil, corn oil and olive oil respectively for miscibility, and then the conditions of miscibility were observed. Specifically, 1) adding 0.50 ml of ethyl lactate for each one into eight vials of 7 ml each, and then adding 0.50 ml of ethyl oleate, glycerol triacetate, benzyl benzoate, castor oil, sesame oil, soybean oil, corn oil and olive oil thereto respectively; swirl them for 5 min to be mixed uniformly, followed by standing for 10 min, and then observing and recording the conditions of miscibility of various solvents; 2) adding 0.30 ml of sesame oil, soybean oil, corn oil, olive oil, ethyl oleate, glycerol triacetate and benzyl benzoate respectively into seven vials of 7 ml each; and then adding 0.30 ml of castor oil and 0.30 ml of ethyl lactate thereto; swirl them for 5 min to be mixed uniformly, followed by standing for 10 min; and then observing and recording the conditions of miscibility of various solvents.

TABLE 2

| | Staticstics of the observed result of miscibility of ethyl lactate with various solvents | | | | | | | |
|---|---|---|---|---|---|---|---|---|
| No. | 1 | 2 | 3 | 4 | 5 | 6 | 7 | 8 |
| Name | ethyl oleate | benzyl benzoate | glycerol triacetate | castor oil | sesame oil | corn oil | olive oil | soybean oil |
| ethyl lactate | miscible | miscible | miscible | miscible | immiscible | immiscible | immiscible | immiscible |

TABLE 3

Statistics of the observed result of miscibility of ethyl lactate with various mixed oils

| Name | mixed oil 1 | mixed oil 2 | mixed oil 3 | mixed oil 4 | mixed oil 5 | mixed oil 6 | mixed oil 7 |
|---|---|---|---|---|---|---|---|
| ethyl lactate | miscible | miscible | miscible | miscible | miscible | miscible | miscible |

Note:
mixed oil 1 is a 1:1 mixture of ethyl oleate and castor oil; mixed oil 2 is a 1:1 mixture of benzyl benzoate and castor oil; mixed oil 3 is a 1:1 mixture of glycerol triacetate and castor oil; mixed oil 4 is a 1:1 mixture of sesame oil and castor oil; mixed oil 5 is a 1:1 mixture of corn oil and castor oil; mixed oil 6 is a 1:1 mixture of olive oil and castor oil; mixed oil 7 is a 1:1 mixture of soybean oil and castor oil.

The experimental results show that each of ethyl oleate, ethyl benzoate, glycerol triacetate, and castor oil is miscible with ethyl lactate; the mixture of castor oil with one of ethyl oleate, ethyl benzoate, glycerol triacetate, sesame oil, olive oil, corn oil and soybean oil is miscible with ethyl lactate.

Experimental Example 3. Experiment of Pharmacal Formulation Stability In Vitro (4° C.)

Based on Experimental example 2, a measurement of dissolution stability of fulvestrant (4° C.) was carried out, specifically, an appropriate amount of fulvestrant raw drug was precisely weighed; under the protection of nitrogen, according to the preferred solvents in Experimental example 2, a cosolvent was firstly added, followed by sequential addition of an analgesic and a dispersant; and then filled with nitrogen and sealed; the formulations were observed for their clarity at 2 hours after production at normal temperature, and the formulations without precipitates were picked out for a preservation of 1-2 days at 4-6° C., and observed continually for their clarity, and the formulations without precipitates were screened out. The specific formulae were as follows:

TABLE 4

Statistics of combinations of some good sustained-release blank formulations

| Cosolvent | Dispersant | Analgesic |
|---|---|---|
| ethyl lactate | castor oil | trichloro-tert-butanol |
| ethyl lactate | castor oil | benzyl alcohol |
| ethyl lactate | mixed oil | trichloro-tert-butanol |
| ethyl lactate | mixed oil | benzyl alcohol |
| ethyl lactate | glycerol triacetate, castor oil | trichloro-tert-butanol |
| ethyl lactate | glycerol triacetate, castor oil | benzyl alcohol |
| ethyl lactate | glycerol triacetate, mixed oil | trichloro-tert-butanol |
| ethyl lactate | glycerol triacetate, mixed oil | benzyl alcohol |
| ethyl lactate | ethyl oleate, castor oil | trichloro-tert-butanol |
| ethyl lactate | ethyl oleate, castor oil | benzyl alcohol |
| ethyl lactate | ethyl oleate, mixed oil | trichloro-tert-butanol |
| ethyl lactate | ethyl oleate, mixed oil | benzyl alcohol |
| ethyl lactate | benzyl benzoate, castor oil | trichloro-tert-butanol |
| ethyl lactate | benzyl benzoate, castor oil | benzyl alcohol |
| ethyl lactate | benzyl benzoate, mixed oil | trichloro-tert-butanol |
| ethyl lactate | benzyl benzoate, mixed oil | benzyl alcohol |

Note:
the mixed oil refers to a mixture of castor oil and soybean oil.

TABLE 5

Statistics of some preferable formulae in the stability experiment of oily formulations of fulvestrant (4° C.) using ethyl lactate as a cosolvent

| No. | Cosolvent | Dispersant | Analgesic | Highest drug concentration |
|---|---|---|---|---|
| 1 | ethyl lactate 5% | ethyl oleate 35%, castor oil 60% | trichloro-tert-butanol 0.3% | 10 mg/ml |
| 2 | ethyl lactate 5% | benzyl benzoate 32%, castor oil 60% | benzyl alcohol 3% | 10 mg/ml |
| 3 | ethyl lactate 5% | glycerol triacetate 35%, castor oil 60% | trichloro-tert-butanol 0.3% | 10 mg/ml |
| 4 | ethyl lactate 10% | ethyl oleate 30%, castor oil 60% | trichloro-tert-butanol 0.3% | 20 mg/ml |
| 5 | ethyl lactate 10% | benzyl benzoate 27%, castor oil 60% | benzyl alcohol 3% | 20 mg/ml |
| 6 | ethyl lactate 10% | glycerol triacetate 30%, castor oil 60% | trichloro-tert-butanol 0.3% | 20 mg/ml |
| 7 | ethyl lactate 15% | ethyl oleate 25%, castor oil 60% | trichloro-tert-butanol 0.3% | 30 mg/ml |
| 8 | ethyl lactate 15% | benzyl benzoate 20%, castor oil 60% | benzyl alcohol 5% | 30 mg/ml |
| 9 | ethyl lactate 15% | glycerol triacetate 35%, castor oil 60% | trichloro-tert-butanol 0.3% | 30 mg/ml |
| 10 | ethyl lactate 20% | ethyl oleate 20%, castor oil 60% | trichloro-tert-butanol 0.3% | 40 mg/ml |
| 11 | ethyl lactate 20% | benzyl benzoate 15%, castor oil 60% | benzyl alcohol 5% | 40 mg/ml |
| 12 | ethyl lactate 20% | glycerol triacetate 20%, castor oil 60% | trichloro-tert-butanol 0.3% | 40 mg/ml |
| 13 | ethyl lactate 25% | glycerol triacetate 15%, castor oil 60% | trichloro-tert-butanol 0.5% | 50 mg/ml |
| 14 | ethyl lactate 25% | glycerol triacetate 10%, castor oil 60% | benzyl alcohol 5% | 50 mg/ml |
| 15 | ethyl lactate 25% | ethyl oleate 15%, castor oil 60% | trichloro-tert-butanol 0.5% | 50 mg/ml |
| 16 | ethyl lactate 25% | ethyl oleate 10%, castor oil 60% | benzyl alcohol 5% | 50 mg/ml |
| 17 | ethyl lactate 25% | benzyl benzoate 15%, castor oil 60% | trichloro-tert-butanol 0.5% | 50 mg/ml |

TABLE 5-continued

Statistics of some preferable formulae in the stability experiment of oily formulations of fulvestrant (4° C.) using ethyl lactate as a cosolvent

| No. | Cosolvent | Dispersant | Analgesic | Highest drug concentration |
|---|---|---|---|---|
| 18 | ethyl lactate 25% | benzyl benzoate 10%, castor oil 65% | benzyl alcohol 5% | 50 mg/ml |
| 19 | ethyl lactate 30% | castor oil 70% | trichloro-tert-butanol 0.5% | 60 mg/ml |
| 20 | ethyl lactate 30% | castor oil 65% | benzyl alcohol 5% | 60 mg/ml |
| 21 | ethyl lactate 50% | castor oil 50% | trichloro-tert-butanol 0.5% | 100 mg/ml |
| 22 | ethyl lactate 50% | castor oil 45% | benzyl alcohol 5% | 100 mg/ml |
| 23 | ethyl lactate 50% | castor oil 50% | trichloro-tert-butanol 0.5% | 100 mg/ml |
| 24 | ethyl lactate 80% | castor oil 15% | benzyl alcohol 5% | 170 mg/ml |
| 25 | ethyl lactate 30% | glycerol triacetate 10%, mixed oil 60% (soybean oil:castor oil, 1:1) | trichloro-tert-butanol 0.5% | 40 mg/ml |
| 26 | ethyl lactate 30% | glycerol triacetate 10%, mixed oil 55% (sesame oil:castor oil, 1:1) | benzyl alcohol 5% | 40 mg/ml |
| 27 | ethyl lactate 30% | ethyl oleate 10%, mixed oil 60% (peanut oil:castor oil, 1:1) | trichloro-tert-butanol 0.5% | 40 mg/ml |
| 28 | ethyl lactate 30% | ethyl oleate 10%, mixed oil 55% (olive oil:castor oil, 1:1) | benzyl alcohol 5% | 40 mg/ml |
| 29 | ethyl lactate 30% | benzyl benzoate 10%, mixed oil 60% (soybean oil:castor oil, 1:1) | trichloro-tert-butanol 0.5% | 40 mg/ml |
| 30 | ethyl lactate 30% | benzyl benzoate 10%, mixed oil 55% (peanut oil:castor oil, 1:1) | benzyl alcohol 5% | 40 mg/ml |
| 31 | ethyl lactate 35% | mixed oil 65% (soybean oil:castor oil, 1:1) | trichloro-tert-butanol 0.5% | 50 mg/ml |
| 32 | ethyl lactate 35% | mixed oil 60% (sesame oil:castor oil, 1:1) | benzyl alcohol 5% | 50 mg/ml |
| 33 | ethyl lactate 50% | mixed oil 50% (soybean oil:castor oil, 1:1) | trichloro-tert-butanol 0.5% | 70 mg/ml |
| 34 | ethyl lactate 50% | mixed oil 45% (peanut oil:castor oil, 1:1) | benzyl alcohol 5% | 70 mg/ml |
| 35 | ethyl lactate 50% | mixed oil 50% (olive oil:castor oil, 1:1) | trichloro-tert-butanol 0.5% | 70 mg/ml |
| 36 | ethyl lactate 80% | mixed oil 15% (soybean oil:castor oil, 1:1) | benzyl alcohol 5% | 110 mg/ml |
| 37 | ethyl lactate 80% | mixed oil 20% (sesame oil:castor oil, 1:1) | trichloro-tert-butanol 0.5% | 110 mg/ml |
| 38 | ethyl lactate 80% | mixed oil 15% (peanut oil:castor oil, 1:1) | benzyl alcohol 5% | 110 mg/ml |

Experimental Example 4. Investigative Experiment of Viscosity

Referring to the preferable formulae screened out in Experimental Examples 2 and 3, an investigative experiment of viscosity in vitro was carried out, specifically, 10 ml of the oily formulations of fulvestrant according to the invention (produced in accordance with the specific formulae in the following table) and commercial fulvestrant formulations (produced in accordance with the formula in the Instructions) were metered; the viscosities of the formulations were tested by NDJ-1 Rotational Viscometer, wherein each sample was tested 6 times, and the results thereof were averaged and accounted; meanwhile, a needle compliance test was performed using 5 ml syringe (containing 0.7 mm needle), at an experimental temperature of 25° C. The detailed results were provided in the table below:

TABLE 6

Investigative experiment of viscosity and formula design for oily formulations of fulvestrant having various concentrations

| No. | Cosolvent | Dispersant | Analgesic | Drug concentration |
|---|---|---|---|---|
| control | ethyl alcohol 10%, benzyl alcohol 10% | benzyl benzoate 15%, castor oil 65% | benzyl alcohol | 50 mg/ml |

TABLE 6-continued

Investigative experiment of viscosity and formula design for oily formulations of fulvestrant having various concentrations

| No. | Cosolvent | Dispersant | Analgesic | Drug concentration |
|---|---|---|---|---|
| formula 1 | ethyl lactate 5% | ethyl oleate 35%, castor oil 60% | trichloro-tert-butanol 0.3% | 10 mg/ml |
| formula 2 | ethyl lactate 10% | ethyl oleate 30%, castor oil 60% | trichloro-tert-butanol 0.3% | 20 mg/ml |
| formula 3 | ethyl lactate 15% | glycerol triacetate 35%, castor oil 60% | trichloro-tert-butanol 0.3% | 30 mg/ml |
| formula 4 | ethyl lactate 20% | glycerol triacetate 20%, castor oil 60% | trichloro-tert-butanol 0.3% | 40 mg/ml |
| formula 5 | ethyl lactate 25% | glycerol triacetate 15%, castor oil 60% | trichloro-tert-butanol 0.5% | 50 mg/ml |
| formula 6 | ethyl lactate 30% | castor oil 70% | trichloro-tert-butanol 0.5% | 60 mg/ml |
| formula 7 | ethyl lactate 50% | castor oil 50% | trichloro-tert-butanol 0.5% | 100 mg/ml |
| formula 8 | ethyl lactate 80% | castor oil 15% | benzyl alcohol 5% | 170 mg/ml |
| formula 9 | ethyl lactate 30% | glycerol triacetate 10%, mixed oil 60% (soybean oil:castor oil, 1:1) | trichloro-tert-butanol 0.5% | 40 mg/ml |
| formula 10 | ethyl lactate 35% | mixed oil 65% (soybean oil:castor oil, 1:1) | trichloro-tert-butanol 0.5% | 50 mg/ml |
| formula 11 | ethyl lactate 50% | mixed oil 45% (peanut oil:castor oil, 1:1) | benzyl alcohol 5% | 70 mg/ml |
| formula 12 | ethyl lactate 80% | mixed oil 20% (sesame oil:castor oil, 1:1) | trichloro-tert-butanol 0.5% | 110 mg/ml |

TABLE 7

Statistics of investigative experiment results of viscosity of oily formulations of fulvestrant ($\bar{x} \pm s$, n = 6)

| Group | Animal number | viscosity value |
|---|---|---|
| control | 6 | 38.80 ± 3.89 |
| formula 1 | 6 | 39.93 ± 4.41 |
| formula 2 | 6 | 38.92 ± 4.28 |
| formula 3 | 6 | 36.90 ± 3.64 |
| formula 4 | 6 | 36.63 ± 3.51 |
| formula 5 | 6 | 37.48 ± 4.42 |
| formula 6 | 6 | 39.73 ± 5.18 |
| formula 7 | 6 | 33.92 ± 2.98 |
| formula 8 | 6 | 18.83 ± 2.45 |
| formula 9 | 6 | 36.27 ± 2.33 |
| formula 10 | 6 | 34.95 ± 2.73 |
| formula 11 | 6 | 29.10 ± 3.62 |
| formula 12 | 6 | 16.90 ± 2.79 |

The experiment results show that as compared with the control group, the formulae 7, 8, 11 and 12 according to the invention have a significantly reduced viscosity in vitro, mainly due to the low content of the dispersant; the other inventive formulae have a viscosity close to that of the control. The need compliance was tested with 5 ml syringe (containing 0.7 mm needle), and the result was good.

Experimental Example 5. Study on Topical Irritation of Intramuscular Injection in Animals Referring to the experimental results of Experimental examples 3 and 4, representative formulae of the oily formulations of fulvestrant at various concentrations according to the invention (see Table 7 for details) were selected for the study on topical irritation of intramuscular injection in animals. 78 female New Zealand White Rabbits (or Japanese White Rabbits) having a weight of 2.0 kg-2.5 kg were acclimated for 2-3 d in the laboratory environment. Subsequently, the left and right hind limbs of all animals were shaved, and then dehaired using a depilatory agent. Next day, the animals were randomly divided into 13 groups according to weight, with 6 ones per group. Each group of animals were injected with 1.2 ml of physiological saline at biceps femoris of left hind limb, and 1.2 ml of the formulation according to the invention at biceps femoris of right hind limb. The animals' responses and the condition of injection sites were observed and recorded at 1 h after injection. The animals' responses and the condition of injection sites were observed and recorded at 24 h after injection. The animals' responses and the condition of injection sites were observed and recorded at 48 h after injection. The animals were then executed, and bicepses femoris at the injection sites were dissected, and excided lengthwise, and then observed for the irritation response at injection sites with naked eyes, and a histopathologic examination was conducted. The observation results with naked eyes were scored in accordance with Table 8.

TABLE 8

Statistics of preferable formulae in irritation experiments

| No. | Cosolvent | Dispersant | Analgesic | Drug concentration |
|---|---|---|---|---|
| control | ethyl alcohol 10%, benzyl alcohol 10% | benzyl benzoate 15%, castor oil 65% | benzyl alcohol | 50 mg/ml |

TABLE 8-continued

Statistics of preferable formulae in irritation experiments

| No. | Cosolvent | Dispersant | Analgesic | Drug concentration |
|---|---|---|---|---|
| formula 1 | ethyl lactate 25% | glycerol triacetate 15%, castor oil 60% | trichloro-tert-butanol 0.5% | 50 mg/ml |
| formula 2 | ethyl lactate 25% | ethyl oleate 10%, castor oil 60% | benzyl alcohol 5% | 50 mg/ml |
| formula 3 | ethyl lactate 30% | castor oil 65% | benzyl alcohol 5% | 60 mg/ml |
| formula 4 | ethyl lactate 50% | castor oil 50% | trichloro-tert butanol 0.5% | 100 mg/ml |
| formula 5 | ethyl lactate 50% | castor oil 45% | benzyl alcohol 5% | 100 mg/ml |
| formula 6 | ethyl lactate 80% | castor oil 15% | benzyl alcohol 5% | 170 mg/ml |
| formula 7 | ethyl lactate 30% | glycerol triacetate 10%, mixed oil 60% (soybean oil:castor oil, 1:1) | trichloro-tert-butanol 0.5% | 40 mg/ml |
| formula 8 | ethyl lactate 30% | ethyl oleate 10%, mixed oil 55% (olive oil:castor oil, 1:1) | benzyl alcohol 5% | 40 mg/ml |
| formula 9 | ethyl lactate 30% | benzyl benzoate 10%, mixed oil 60% (sesame oil:castor oil, 1:1) | trichloro-tert-butanol 0.5% | 40 mg/ml |
| formula 10 | ethyl lactate 35% | mixed oil 65% (soybean oil:castor oil, 1:1) | trichloro-tert - butanol 0.5% | 50 mg/m |
| formula 11 | ethyl lactate 50% | mixed oil 45% (peanut oil:castor oil, 1:1) | benzyl alcohol 5% | 70 mg/ml |
| formula 12 | ethyl lactate 80% | mixed oil 15% (soybean oil:castor oil, 1:1) | benzyl alcohol 5% | 110 mg/ml |

TABLE 9

Criteria for scoring topical irritation response of intramuscular injection

| Response grade | Irritation response |
|---|---|
| 0 | No obvious change |
| 1 | Slight hyperemia, with the range < 0.5 cm × 1.0 cm |
| 2 | Moderate hyperemia, with the scope > 0.5 cm × 1.0 cm |
| 3 | Severe hyperemia, accompanied by muscle degeneration |
| 4 | Appearance of necrosis, with brown degeneration |
| 5 | Appearance of extensive necrosis |

TABLE 10

Statistics of experiment results about topical irritation of intramuscular injection of oily formulations of fulvestrant in animals ($\bar{x} \pm s$, n = 6)

| Group | Animal number | Score of irritation |
|---|---|---|
| control | 6 | 1.42 ± 0.49 |
| formula 1 | 6 | 0.92 ± 0.38 |
| formula 2 | 6 | 0.75 ± 0.42 |
| formula 3 | 6 | 0.92 ± 0.38 |
| formula 4 | 6 | 1.33 ± 0.52 |
| formula 5 | 6 | 1.42 ± 0.49 |
| formula 6 | 6 | 1.92 ± 0.80 |
| formula 7 | 6 | 0.92 ± 0.49 |
| formula 8 | 6 | 0.83 ± 0.52 |
| formula 9 | 6 | 0.92 ± 0.49 |
| formula 10 | 6 | 0.92 ± 0.49 |
| formula 11 | 6 | 1.50 ± 0.63 |
| formula 12 | 6 | 1.83 ± 0.61 |

The experimental results show that as for the topical intramuscular injection of oily formulations of fulvestrant having different formulae in animals, the scores of irritation of formulae 6 and 12 are significantly higher than that of the control, the scores of irritation of formulae 5 and 11 are similar to that of the control, and the score of irritation of each of other formulae is lower than that of the control. The experimental results may reflect that the irritation of intramuscular injection of glycerol triacetate, ethyl oleate, benzyl benzoate, soybean oil, castor oil, sesame oil, corn oil and the like is slight, and upon intramuscularly injected, ethyl lactate has a certain degree of irritation and appears to have a dose-effect relationship. When the content of ethyl lactate is lower than 50%, the irritation is weak; and when the content of ethyl lactate is more than 50%, the irritation of topical intramuscular injection increases significantly.

Experimental Example 9. In Vivo Pharmacokinetics Experiment I in Animals 70 female SD rats weighed 200-220 g were acclimated for 2-3 days, and then randomly divided into 7 groups with 10 rats each. Specific names and formulae are shown below. According to the design of groups, each rat in every group was deeply injected with 0.2 ml of solution of corresponding formula at lateral gastrocnemius of right hind limb (the rat in each group was administrated according to 200 g of body weight). The administration sites were then pressed lightly for 1-2 min to prevent the outflow of the solution. After administration, the time of administration was recorded. At 2 h, 6 h, 1 d, 3 d, 7 d, 14 d, 21 d, 28 d, 31 d before and after the administration respectively, 0.3 ml of blood was taken from orbital vein in a rat to a heparinized tube. After centrifuging at 3500 rpm for 10 min, 0.1 ml of serum was taken quantitatively and the concentration of fulvestrant in the blood sample was measured using LS-MS-MS. The specific numerical values are provided below. A curve of blood concentration versus time was shown in FIG. 1.

TABLE 11

Group design (I) for in vivo pharmacokinetics experiment in animals

| No. | Cosolvent | Dispersant | Analgesic | Drug concentration |
|---|---|---|---|---|
| control | ethyl alcohol 10%, benzyl alcohol 10% | benzyl benzoate 15%, castor oil 65% | — | 50 mg/ml |
| formula 1 | ethyl lactate 25% | glycerol triacetate 15%, castor oil 60% | trichloro-tert-butanol 0.5% | 50 mg/ml |
| formula 2 | ethyl lactate 25% | ethyl oleate 10%, castor oil 60% | benzyl alcohol 5% | 50 mg/ml |
| formula 3 | ethyl lactate 50% | castor oil 50% | trichloro-tert-butanol 0.5% | 100 mg/ml |
| formula 4 | ethyl lactate 35% | mixed oil 65% (soybean oil:castor oil, 1:1) | trichloro-tert-butanol 0.5% | 50 mg/ml |
| formula 5 | ethyl lactate 35% | mixed oil 65% (soybean oil:castor oil, 1:1) | trichloro-tert-butanol 0.5% | 50 mg/ml |
| formula 6 | ethyl lactate 50% | mixed oil 45% (peanut oil:castor oil, 1:1) | benzyl alcohol 5% | 70 mg/ml |

TABLE 12

Statistics of in vivo blood concentration at different time points in rats following intramuscular injection of fulvestrant formulations of various fomulae ($\bar{x} \pm s$, n = 10)

| Time (h) | control | formula 1 | formula 2 | formula 3 | formula 4 | formula 5 | formula 6 |
|---|---|---|---|---|---|---|---|
| 2 | 6.04 ± 2.57 | 6.69 ± 2.80 | 5.15 ± 2.41 | 7.92 ± 2.03 | 12.77 ± 4.53 | 14.93 ± 3.57 | 14.95 ± 3.97 |
| 12 | 11.43 ± 4.29 | 10.33 ± 3.37 | 9.87 ± 2.14 | 14.58 ± 3.45 | 18.86 ± 6.00 | 21.05 ± 7.29 | 24.04 ± 3.73 |
| 24 | 15.60 ± 3.12 | 18.12 ± 3.77 | 14.50 ± 3.09 | 28.37 ± 8.15 | 36.99 ± 8.47 | 37.93 ± 7.32 | 43.36 ± 3.45 |
| 72 | 21.58 ± 5.84 | 24.94 ± 5.63 | 21.26 ± 4.40 | 39.68 ± 11.70 | 34.25 ± 8.76 | 29.79 ± 9.02 | 39.19 ± 4.81 |
| 168 | 16.60 ± 4.40 | 16.56 ± 3.85 | 16.95 ± 4.16 | 26.64 ± 9.52 | 19.76 ± 4.26 | 26.02 ± 9.89 | 30.89 ± 5.64 |
| 360 | 17.20 ± 4.09 | 14.45 ± 4.03 | 12.02 ± 2.84 | 20.75 ± 4.91 | 13.86 ± 3.33 | 12.38 ± 2.13 | 22.29 ± 8.26 |
| 744 | 5.96 ± 2.50 | 8.19 ± 2.91 | 8.19 ± 3.17 | 14.64 ± 5.72 | 8.21 ± 4.64 | 8.96 ± 4.65 | 14.24 ± 3.44 |

The experimental results show that each formula of oily formulations of fulvestrant shows a good sustained release effect after administration; at 31 d after administration through intramuscular injection, the tested blood concentration was still above effective blood concentration. The features of the pharmacokinetic curve of formulae 1 and 2 of the invention are similar as those of the control. As compared with the control, the blood concentration value at each time point of formula 3 of the invention has an increase, and the blood concentration value at 31 d after administration is 2-3 times as that of the control, presenting a good sustained release effect.

Figure 2:
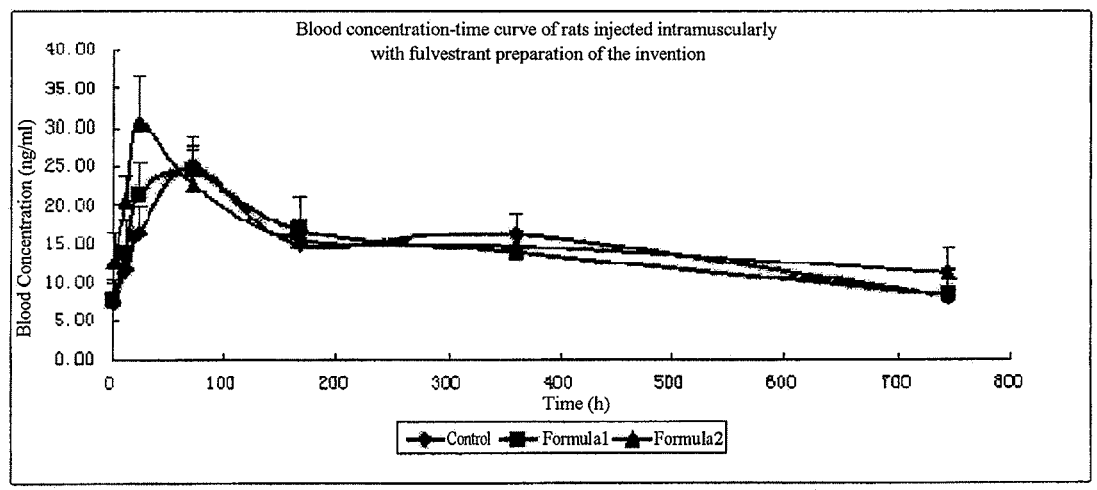
FIG. 2: A curve of blood concentration versus time.

Experimental Example 10. In Vivo Pharmacokinetics Experiment II in Animals 30 female SD rats weighed 200-220 g were acclimated for 2-3 days, and then randomly divided into 3 groups with 10 rats each. Specific names and formulae are shown in Table 13. According to the design of groups, the dosing amount for each rat was 50 mg/kg, and the dosing volume is calculated according to actual body weight. The administration route was a deep and slow injection at lateral gastrocnemius of right hind limb. The injection sites were then pressed lightly for 1-2 min to prevent the outflow of the solution. After administration, the time of the administration was recorded. At 2 h, 6 h, 1 d, 3 d, 7 d, 14 d, 21 d, 28 d, 31 d before and after the administration respectively, 0.3 ml of blood was taken from orbital vein in a rat to a heparinized tube. After centrifuging at 3500 rpm for 10 min, 0.1 ml of serum was taken quantitatively and the concentration of fulvestrant in the blood sample was measure using LS-MS-MS. The specific numerical values were provided below. A curve of blood concentration versus time was shown in FIG. 2.

TABLE 13

Group design (II) for in vivo pharmacokinetics experiment in animals

| No. | Cosolvent | Dispersant | Analgesic | Drug concentration |
|---|---|---|---|---|
| control | ethyl alcohol 10%, benzyl alcohol 10% | benzyl benzoate 15%, castor oil 65% | benzyl alcohol | 50 mg/ml |
| formula 1 | ethyl lactate 50% | castor oil 50% | trichloro-tert-butanol 0.5% | 100 mg/ml |
| formula 2 | ethyl lactate 50% | mixed oil 45% (soybean oil:castor oil, 1:1) | benzyl alcohol 5% | 70 mg/ml |

TABLE 14

Statistics (II) of in vivo blood concentration at different time points in rats following intramuscular injection of fulvestrant formulations of various fomulae ($\bar{x} \pm s$, n = 10)

| Time (h) | control | formula 1 | formula 2 |
|---|---|---|---|
| 2 | 7.43 ± 2.54 | 8.00 ± 2.44 | 12.86 ± 3.66 |
| 12 | 11.71 ± 2.32 | 13.84 ± 4.18 | 20.65 ± 3.36 |

TABLE 14-continued

Statistics (II) of in vivo blood concentration at different time points in rats following intramuscular injection of fulvestrant formulations of various fomulae ($\bar{x} \pm s$, n = 10)

| Time (h) | control | formula 1 | formula 2 |
|---|---|---|---|
| 24 | 16.45 ± 3.40 | 21.49 ± 3.96 | 30.75 ± 5.94 |
| 72 | 24.92 ± 3.83 | 24.43 ± 2.60 | 22.70 ± 5.06 |
| 168 | 15.02 ± 3.08 | 16.87 ± 4.26 | 15.66 ± 2.72 |
| 360 | 16.32 ± 2.73 | 13.98 ± 2.75 | 14.81 ± 1.95 |
| 744 | 8.30 ± 3.63 | 8.45 ± 3.19 | 11.40 ± 3.01 |

The experimental results show that formulae 1 and 2 shows a good sustained release effect within 31 days after administration; as compared with the control, the blood concentration of formula 2 at 12 h after administration through intramuscular injection increases significantly and shows a significant difference (P<0.01), and its peak time is at about 24 h after administration, which is approximately 48 h earlier than that of the control (peak time=72 h); at 31 d after administration, the blood concentration of formula 2 is 11.40 ng/ml, which increases remarkably and shows a significant difference (P<0.05) as compared with the control; and the features of the pharmacokinetic curve of formula 1 are similar as those of the control.

Example 1

Formula:

| Components | Drug proportion |
|---|---|
| fulvestrant | 10 mg |
| ethyl lactate | 0.05 ml |
| Vitamin E acetate (optional) | 3 mg |
| trichloro-tert-butanol | 3 mg |
| glycerol triacetate | 0.35 ml |
| castor oil | balanced to 1 ml |

10 mg of fulvestrant raw drug, 3 mg of trichloro-tert-butanol and 3 mg of Vitamin E acetate (optional) were dissolved in 0.05 ml of ethyl lactate solvent, and sonicated or swirled to facilitate dissolution. When the substances were completely dissolved, 0.35 ml of glycerol triacetate was added and mixed uniformly by swirl, and then castor oil was added to reach 1 ml. It was mixed for 30 min by ultrasound or swirl, passed through a 0.45 μm organic membrane/nylon membrane under a sterile condition to remove impurities, sterilized through a 0.22 μm organic membrane/nylon membrane, filled with sterilized nitrogen, plugged and capped, to obtain an oily formulation of fulvestrant.

Example 2

Formula:

| Components | Drug proportion |
|---|---|
| fulvestrant | 170 mg |
| ethyl lactate | 0.80 ml |
| Vitamin E acetate (optional) | 5 mg |
| benzyl alcohol | 50 μl |
| castor oil | balanced to 1 ml |

170 mg of fulvestrant raw drug, 50 μl of benzyl alcohol and 5 mg of Vitamin E acetate (optional) were dissolved in 0.80 ml of ethyl lactate solvent, and sonicated or swirled for 30 min to facilitate dissolution. When the substances were completely dissolved, castor oil was added to reach 1 ml. It was mixed for 10 min by ultrasound or swirl, passed through a 0.45 μm organic membrane/nylon membrane under a sterile condition to remove impurities, sterilized through a 0.22 μm organic membrane/nylon membrane, filled with sterilized nitrogen, plugged and capped, to obtain an oily formulation of fulvestrant.

Example 3

Formula:

| Components | Drug proportion |
|---|---|
| fulvestrant | 25 mg |
| ethyl lactate | 0.15 ml |
| Vitamin E acetate (optional) | 5 mg |
| trichloro-tert-butanol | 3 mg |
| ethyl oleate | 0.25 ml |
| castor oil | balanced to 1 ml |

25 mg of fulvestrant raw drug, 3 mg of trichloro-tert-butanol and 5 mg of Vitamin E acetate (optional) were dissolved in 0.15 ml of ethyl lactate solvent, and sonicated or swirled for 30 min to facilitate dissolution. When the substances were completely dissolved, 0.25 ml of ethyl oleate was added and mixed uniformly by swirl, and then castor oil was added to reach 1 ml. It was mixed for 10 min by ultrasound or swirl, passed through a 0.45 μm organic membrane/nylon membrane under a sterile condition to remove impurities, sterilized through a 0.22 μm organic membrane/nylon membrane, filled with sterilized nitrogen, plugged and capped, to obtain an oily formulation of fulvestrant.

Example 4

Formula:

| Components | Drug proportion |
|---|---|
| fulvestrant | 60 mg |
| ethyl lactate | 0.30 ml |
| Vitamin E acetate (optional) | 5 mg |
| benzyl alcohol | 50 μl |
| castor oil | balanced to 1 ml |

60 mg of fulvestrant raw drug, 50 μl of benzyl alcohol and 5 mg of Vitamin E acetate (optional) were dissolved in 0.30 ml of ethyl lactate solvent, and sonicated or swirled to facilitate dissolution. When the substances were completely dissolved, castor oil was added to reach 1 ml. It was mixed for 10 min by ultrasound or swirl, passed through a 0.45 μm organic membrane/nylon membrane under a sterile condition to remove impurities, sterilized through a 0.22 μm organic membrane/nylon membrane, filled with sterilized nitrogen, plugged and capped, to obtain an oily formulation of fulvestrant.

Example 5

Formula:

| Components | Drug proportion |
| --- | --- |
| fulvestrant | 100 mg |
| ethyl lactate | 0.50 ml |
| Vitamin E acetate (optional) | 5 mg |
| benzyl alcohol | 50 µl |
| castor oil | balanced to 1 ml |

100 mg of fulvestrant raw drug, 50 µl of benzyl alcohol and 5 mg of Vitamin E acetate (optional) were dissolved in 0.50 ml of ethyl lactate solvent, and sonicated or swirled for 30 min to facilitate dissolution. When the substances were completely dissolved, castor oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 6

Formula:

| Components | Drug proportion |
| --- | --- |
| fulvestrant | 50 mg |
| ethyl lactate | 0.25 ml |
| Vitamin E acetate (optional) | 5 mg |
| benzyl alcohol | 50 µl |
| castor oil | balanced to 1 ml |

50 mg of fulvestrant raw drug, 50 µl of benzyl alcohol and 5 mg of Vitamin E acetate (optional) were dissolved in 0.25 ml of ethyl lactate solvent, and sonicated or swirled for 30 min to facilitate dissolution. When the substances were completely dissolved, castor oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 7

Formula:

| Components | Drug proportion |
| --- | --- |
| fulvestrant | 50 mg |
| ethyl lactate | 0.35 ml |
| Vitamin E acetate (optional) | 5 mg |
| trichloro-tert-butanol | 5 mg |
| mixed oil (soybean oil:castor oil = 1:1) | balanced to 1 ml |

50 mg of fulvestrant raw drug, 5 mg of trichloro-tert-butanol and 5 mg of Vitamin E acetate (optional) were dissolved in 0.35 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 8

Formula:

| Components | Drug proportion |
| --- | --- |
| fulvestrant | 50 mg |
| ethyl lactate | 0.35 ml |
| Vitamin E acetate (optional) | 5 mg |
| trichloro-tert-butanol | 5 mg |
| mixed oil (olive oil:castor oil = 1:1) | balanced to 1 ml |

50 mg of fulvestrant raw drug, 5 mg of trichloro-tert-butanol and 5 mg of Vitamin E acetate (optional) were dissolved in 0.35 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 9

Formula:

| Components | Drug proportion |
| --- | --- |
| fulvestrant | 50 mg |
| ethyl lactate | 0.35 ml |
| Vitamin E acetate (optional) | 5 mg |
| trichloro-tert-butanol | 5 mg |
| mixed oil (sesame oil:castor oil = 1:1) | balanced to 1 ml |

50 mg of fulvestrant raw drug, 5 mg of trichloro-tert-butanol and 5 mg of Vitamin E acetate (optional) were dissolved in 0.35 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 10

Formula:

| Components | Drug proportion |
| --- | --- |
| fulvestrant | 70 mg |
| ethyl lactate | 0.50 ml |
| Vitamin E acetate (optional) | 5 mg |
| trichloro-tert-butanol | 5 mg |
| mixed oil (soybean oil:castor oil = 1:1) | balanced to 1 ml |

70 mg of fulvestrant raw drug, 5 mg of trichloro-tert-butanol and 5 mg of Vitamin E acetate (optional) were dissolved in 0.50 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 11

Formula;

| Components | Drug proportion |
|---|---|
| fulvestrant | 70 mg |
| ethyl lactate | 0.50 ml |
| Vitamin E acetate (optional) | 5 mg |
| trichloro-tert-butanol | 5 mg |
| mixed oil (olive oil:castor oil = 1:1) | balanced to 1 ml |

70 mg of fulvestrant raw drug, 5 mg of trichloro-tert-butanol and 5 mg of Vitamin E acetate (optional) were dissolved in 0.50 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 12

Formula:

| Components | Drug proportion |
|---|---|
| fulvestrant | 70 mg |
| ethyl lactate | 0.50 ml |
| Vitamin E acetate (optional) | 5 mg |
| trichloro-tert-butanol | 5 mg |
| mixed oil (corn oil:castor oil = 1:1) | balanced to 1 ml |

70 mg of fulvestrant raw drug, 5 mg of trichloro-tert-butanol and 5 mg of Vitamin E acetate (optional) were dissolved in 0.50 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 13

Formula:

| Components | Drug proportion |
|---|---|
| fulvestrant | 110 mg |
| ethyl lactate | 0.80 ml |
| Vitamin E acetate (optional) | 5 mg |
| trichloro-tert-butanol | 5 mg |
| mixed oil (soybean oil:castor oil = 1:1) | balanced to 1 ml |

110 mg of fulvestrant raw drug, 5 mg of trichloro-tert-butanol and 5 mg of Vitamin E acetate (optional) were dissolved in 0.80 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 14

Formula:

| Components | Drug proportion |
|---|---|
| fulvestrant | 110 mg |
| ethyl lactate | 0.80 ml |
| Vitamin E acetate (optional) | 5 mg |
| benzyl alcohol | 50 µl |
| mixed oil (corn oil:castor oil = 1:1) | balanced to 1 ml |

110 mg of fulvestrant raw drug, 5 mg of trichloro-tert-butanol and 5 mg of Vitamin E acetate (optional) were dissolved in 0.80 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 15

Formula:

| Components | Drug proportion |
|---|---|
| fulvestrant | 110 mg |
| ethyl lactate | 0.80 ml |
| Vitamin E acetate (optional) | 5 mg |
| trichloro-tert-butanol | 5 mg |
| mixed oil (sesame oil:castor oil = 1:1) | balanced to 1 ml |

110 mg of fulvestrant raw drug, 5 mg of trichloro-tert-butanol and 5 mg of Vitamin E acetate (optional) were dissolved in 0.80 ml of ethyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 µm organic membrane/nylon membrane under a sterile condition to remove impurities, sterilized through a 0.22 µm organic membrane/nylon membrane, filled with sterilized nitrogen, plugged and capped, to obtain an oily formulation of fulvestrant.

Example 16

Formula:

| Components | Drug proportion |
| --- | --- |
| fulvestrant | 50 mg |
| butyl lactate | 0.30 ml |
| Vitamin E acetate (optional) | 5 mg |
| trichloro-tert-butanol | 5 mg |
| glycerol triacetate | 0.10 ml |
| castor oil | balanced to 1 ml |

50 mg of fulvestrant raw drug, 5 mg of trichloro-tert-butanol, 0.10 ml of glycerol triacetate and 5 mg of Vitamin E acetate (optional) were dissolved in 0.30 ml of butyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 μm organic membrane/nylon membrane under a sterile condition to remove impurities, sterilized through a 0.22 μm organic membrane/nylon membrane, filled with sterilized nitrogen, plugged and capped, to obtain an oily formulation of fulvestrant.

Example 17

Formula:

| Components | Drug proportion |
| --- | --- |
| fulvestrant | 75 mg |
| butyl lactate | 0.40 ml |
| Vitamin E acetate (optional) | 5 mg |
| benzyl alcohol | 50 μl |
| castor oil | balanced to 1 ml |

75 mg of fulvestrant raw drug, 50 μl of benzyl alcohol and 5 mg of Vitamin E acetate (optional) were dissolved in 0.40 ml of butyl lactate solvent, and sonicated or swirled for 30 min to facilitate dissolution. When the substances were completely dissolved, castor oil was added to reach 1 ml. It was mixed for 10 min by ultrasound or swirl, passed through a 0.45 μm organic membrane/nylon membrane under a sterile condition to remove impurities, sterilized through a 0.22 μm organic membrane/nylon membrane, filled with sterilized nitrogen, plugged and capped, to obtain an oily formulation of fulvestrant.

Example 18

Formula:

| Components | Drug porportion |
| --- | --- |
| fulvestrant | 45 mg |
| butyl lactate | 0.40 ml |
| Vitamin E acetate (optional) | 5 mg |
| trichloro-tert-butanol | 5 mg |
| mixed oil (soybean oil:castor oil = 1:1) | balanced to 1 ml |

45 mg of fulvestrant raw drug, 5 mg of trichloro-tert-butanol and 5 mg of Vitamin E acetate (optional) were dissolved in 0.40 ml of butyl lactate solvent, and sonicated or swirled for 30 min to facilitate dissolution. When the substances were completely dissolved, mixed oil was added to reach 1 ml. It was mixed for 10 min by ultrasound or swirl, passed through a 0.45 μm organic membrane/nylon membrane under a sterile condition to remove impurities, sterilized through a 0.22 μm organic membrane/nylon membrane, filled with sterilized nitrogen, plugged and capped, to obtain an oily formulation of fulvestrant.

We claim:

1. An oily formulation of fulvestrant or derivatives thereof, characterized in that, the formulation comprises per ml:
    (a) fulvestrant or derivatives thereof, 10 to 170 mg;
    (b) ethyl lactate, 0.15 to 0.80 ml;
    (c) an analgesic, 3 to 5 mg/30 to 50 μl; and
    (d) a dispersant, balanced to 1 ml,
    wherein said fulvestrant or derivatives thereof has the following structure:

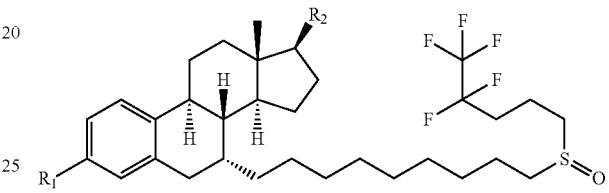

wherein
1) both of $R_1$ and $R_2$ are —OH; or
2) one of $R_1$ and $R_2$ is —H, and the other one is —OH; and
one, or a mixture of two or more of fulvestrant or derivatives thereof may be used in the formulation, and wherein the dispersant comprises a combination of glycerol triacetate and castor oil.

2. The oily formulation according to claim 1, characterized in that, the formulation comprises per ml:
    (a) fulvestrant or derivatives thereof, 25 to 100 mg;
    (b) ethyl lactate, 0.30 to 0.50 ml;
    (c) an analgesic, 3 to 5 mg/30-50 μl; and
    (d) a dispersant, balanced to 1 ml.

3. The formulation according to claim 1, characterized in that, the analgesic is selected from one, or a mixture of two or more of benzyl alcohol, trichloro-tert-butanol, lidocaine (free base), procaine (free base), tetracaine (free base), ropivacaine (free base), mepivacaine (free base), articaine (free base), bupivacaine (free base), propofol, propofol derivatives, tramadol, lappaconitine, L-tetrahydropalmatine, pentazocine, cyclobutylmethyl dihydroxymorphina, fentanyl and derivatives thereof.

4. The formulation according to claim 1, characterized in that, the formulae thereof are as follows:

| Cosolvent | Dispersant | Analgesic |
| --- | --- | --- |
| ethyl lactate | castor oil | trichloro-tert-butanol |
| ethyl lactate | castor oil | benzyl alcohol |
| ethyl lactate | mixed oil | trichloro-tert-butanol |
| ethyl lactate | mixed oil | benzyl alcohol |
| ethyl lactate | glycerol triacetate, castor oil | trichloro-tert-butanol |
| ethyl lactate | glycerol triacetate, castor oil | benzyl alcohol |
| ethyl lactate | glycerol triacetate, mixed oil | trichloro-tert-butanol |
| ethyl lactate | glycerol triacetate, mixed oil | benzyl alcohol |
| ethyl lactate | ethyl oleate, castor oil | trichloro-tert-butanol |
| ethyl lactate | ethyl oleate, castor oil | benzyl alcohol |
| ethyl lactate | ethyl oleate, mixed oil | trichloro-tert-butanol |
| ethyl lactate | ethyl oleate, mixed oil | benzyl alcohol |
| ethyl lactate | benzyl benzoate, castor oil | trichloro-tert-butanol |

| Cosolvent | Dispersant | Analgesic |
|---|---|---|
| ethyl lactate | benzyl benzoate, castor oil | benzyl alcohol |
| ethyl lactate | benzyl benzoate, mixed oil | trichloro-tert-butanol |
| ethyl lactate | benzyl benzoate, mixed oil | benzyl alcohol | wherein said mixed oil refers to a mixture of castor oil with one, two or more of soybean oil, sesame oil, corn oil, and olive oil.

5. An oily formulation of fulvestrant, characterized in that, the formulation comprises per ml:
(a) fulvestrant, 10 mg;
(b) ethyl lactate, 0.05 ml;
(c) trichloro-tert-butanol, 3 mg;
(d) glycerol triacetate, 0.35 ml; and
(e) castor oil, balanced to 1 ml.

* * * * *

UNITED STATES PATENT AND TRADEMARK OFFICE
CERTIFICATE OF CORRECTION

PATENT NO. : 10,568,890 B2
APPLICATION NO. : 14/389532
DATED : February 25, 2020
INVENTOR(S) : Lu et al.

Page 1 of 1

It is certified that error appears in the above-identified patent and that said Letters Patent is hereby corrected as shown below:

In the Claims

Column 28 and 29, Lines 51-10:
Claim 4 should appear as follows:
"The formulation according to claim 1, characterized in that, the formulae thereof are as follows:

| Cosolvent | Dispersant | Analgesic |
| --- | --- | --- |
| ethyl lactate | glycerol triacetate, castor oil | trichloro-tert-butanol |
| ethyl lactate | glycerol triacetate, castor oil | benzyl alcohol |
| ethyl lactate | glycerol triacetate, mixed oil | trichloro-tert-butanol |
| ethyl lactate | glycerol triacetate, mixed oil | benzyl alcohol | wherein said mixed oil refers to a mixture of castor oil with one, two or more of soybean oil, sesame oil, corn oil, and olive oil."

Signed and Sealed this
Nineteenth Day of May, 2020

Andrei Iancu
*Director of the United States Patent and Trademark Office*